United States Patent
Saitou

(10) Patent No.: US 8,827,966 B2
(45) Date of Patent: Sep. 9, 2014

(54) SKIN PATCH INSTRUMENT FOR TREATING PAIN

(75) Inventor: Norio Saitou, Shizuoka (JP)

(73) Assignee: Soukenbi Corporation, Shizuoka (JP)

(*) Notice: Subject to any disclaimer, the term of this patent is extended or adjusted under 35 U.S.C. 154(b) by 252 days.

(21) Appl. No.: 12/988,686

(22) PCT Filed: Apr. 30, 2008

(86) PCT No.: PCT/JP2008/058281
§ 371 (c)(1),
(2), (4) Date: Nov. 9, 2010

(87) PCT Pub. No.: WO2009/133610
PCT Pub. Date: Nov. 5, 2009

(65) Prior Publication Data
US 2011/0046580 A1    Feb. 24, 2011

(51) Int. Cl.
*A61M 35/00* (2006.01)
*A61N 1/30* (2006.01)
*A61F 13/00* (2006.01)
*A61F 13/02* (2006.01)
*A61B 17/00* (2006.01)

(52) U.S. Cl.
CPC ..... *A61F 13/023* (2013.01); *A61F 2013/00919* (2013.01); *A61F 2013/00936* (2013.01)
USPC ............. 604/290; 604/19; 604/289; 604/304; 604/307; 606/1; 606/201; 606/204

(58) Field of Classification Search
CPC .................................................. A61H 39/04
See application file for complete search history.

(56) References Cited

U.S. PATENT DOCUMENTS

| | | | | |
|---|---|---|---|---|
| 3,886,939 A | * | 6/1975 | Boxer | 604/290 |
| 3,987,787 A | * | 10/1976 | Boxer | 128/898 |
| 4,022,189 A | * | 5/1977 | Boxer | 600/15 |
| 5,531,675 A | * | 7/1996 | Yoo | 604/20 |
| 5,792,176 A | * | 8/1998 | Chang | 606/204 |
| 6,030,408 A | * | 2/2000 | Kramer | 606/204 |
| D423,676 S | * | 4/2000 | Lazio | D24/214 |
| 6,241,693 B1 | * | 6/2001 | Lambden | 601/15 |

(Continued)

FOREIGN PATENT DOCUMENTS

| | | | | |
|---|---|---|---|---|
| JP | 10-099406 | * | 4/1998 | ............ A61H 39/04 |
| JP | 2004-275750 | | 10/2004 | |

(Continued)

OTHER PUBLICATIONS

English translation of International Search Report for corresponding International Patent Application No. PCT/JP2008/058281 dated Jun. 18, 2008 (4 pages).

*Primary Examiner* — (Jackie) Tan-Uyen T Ho
*Assistant Examiner* — Eric Bryant
(74) *Attorney, Agent, or Firm* — Kilyk & Bowersox, P.L.L.C.

(57) ABSTRACT

A therapeutic patch for treating pain capable of compressing a tender area up to a boundary thereof and/or an entire induration with metallic grains or crushed stones by a treatment method in accordance with a classification determined after clarifying a site of pain by pressing a skin with a pressing bar or fingers (first to fourth fingers) to classify the cause of pain, thereby finding the presence of a geographical tender area and/or the presence of an induration on a skin as the cause of pain.

7 Claims, 10 Drawing Sheets

(56) References Cited

U.S. PATENT DOCUMENTS 6,257,785 B1 * 7/2001 Otten et al. .................. 401/7
2006/0015052 A1 * 1/2006 Crisp ............................ 602/41
2008/0063736 A1 * 3/2008 Kim ............................ 424/740

FOREIGN PATENT DOCUMENTS

| JP | 2005-087495 |   | 4/2005 |
| JP | 2005-087495 | * | 7/2005 |
| JP | 3129267 |   | 1/2007 |

* cited by examiner

FIG. 13A VAS (FIRST TIME) BEFORE AND AFTER TREATMENT

VERTICAL AXIS: VAS(%) HORIZONTAL AXIS: PATIENT NO

FIG. 13B VAS (THIRD TIME) BEFORE AND AFTER TREATMENT

VERTICAL AXIS: VAS(%) HORIZONTAL AXIS: PATIENT NO.

SKIN PATCH INSTRUMENT FOR TREATING PAIN

This application is a National Stage Application of PCT/JP2008/058281, filed Apr. 30, 2008.

BACKGROUND OF THE INVENTION

1. Field of the Invention

The present invention relates to a therapeutic patch for treating pain capable of alleviating pain dramatically by compression with metallic grains or crushed stones by a treatment method in accordance with a classification of a cause of pain into tenderness, an induration, or both of the tenderness and the induration determined after clarifying the cause of pain by pressing with a pressing bar or fingers (mainly, a thumb). The present invention has been made based on the finding of the presence of a geographical boundary in a tender area and/or the presence of an induration on a skin as the cause of pain.

2. Description of the Related Art

In a human body, autonomous nerves are disturbed due to emotional internal factors such as extreme stress and overfatigue caused by pressure of work, which causes a neurological disorder or neurological deterioration. Further, the nerves may also be damaged due to external factors such as sprain.

Further, the control of a muscle is also disturbed due to the neurological disorder, deterioration, or damage, which deteriorates the muscle to cause an induration of muscle fibers.

The neurological disorder, deterioration, or damage, and muscle induration cause pain. The neurological disorder, deterioration, or damage, and muscle induration may be shallow and narrow, or may be deep and wide. Thus, in order to alleviate pain, it is necessary to ameliorate the neurological disorder, deterioration, or damage, and muscle induration, etc. in accordance with the condition.

In order to ameliorate the neurological disorder, deterioration, or damage, and muscle induration, etc., a method of alleviating pain by the administration of a painkiller or a drug in Western medicine or by the acupuncture or moxa cautery in Oriental medicine has been used. However, as the specific cause of pain has not been clarified, treatment is currently conducted unthinkingly with respect to a portion in which a patient complains of particularly strong pain subjectively or a nerve block (upper nerve), i.e., a so-called route or point in Oriental medicine, a tender point, etc.

Further, as simple amelioration means, there are known massage, rest, icing, compression, elevation, etc.

The "massage" refers to flexing "stiffness" that is an induration part.

The "rest" refers to the static treatment of allowing a tissue to recover by fixing a damaged part or preventing the risk of causing damage.

The "icing" refers to applying a cold pack or an ice pack to the periphery of an affected part to allow a blood vessel to contract.

The "compression" refers to fixing a site of pain to bring about a rest.

The "elevation" refers to elevating a damaged site to accelerate a blood flow returning to a heart to reduce the accumulation of body fluid.

However, according to these amelioration means, a human body's capacity to heal is merely expected, and hence, it takes a long period of time for full healing. Further, in some cases, these amelioration means may cause chronicity.

As more simple amelioration means, there is a therapeutic patch for a skin that can be used at home. For example, a therapeutic patch is known, in which a composite granular matter including a metallic solid material formed of powder of pure gold, etc. and an ore material containing 75% or more of a quartz component is fixed to a central part of a pressure-sensitive adhesive sheet with the former located outside and the latter located inside (Japanese Patent Application Laid-open No. 2002-209973).

The object of the therapeutic patch is as follows. That is, when the therapeutic patch is attached to a route or a point of a human body, the thermal function of a far infrared radiation and the energy of minus ions act on the route or the point directly, the radiation and ions being generated from the ore material, etc. of the composite granular matter located at the central part of the sheet.

SUMMARY OF THE INVENTION

The present invention provides a therapeutic patch for treating pain capable of alleviating pain dramatically by compression with metallic grains or crushed stones by a treatment method in accordance with a classification of a cause of pain into tenderness, an induration, or both of the tenderness and the induration determined after clarifying the cause of pain by pressing or palpating a skin with a pressing bar or fingers (mainly, a thumb), based on the finding of the presence of a geographical boundary in a tender area on a skin and/or the presence of an induration as the cause of pain.

In order to solve the above-mentioned problems, the inventors of the present invention et al. pressed an affected part (tender site) in which a patient complains of pain subjectively with a pressing bar or fingers (first to fourth fingers). As a result, the inventors have found that tenderness exhibit a geographical shape instead of a point shape, and there is a boundary therein (boundary between a portion in which the patient feels pain and a portion in which the patient feels no pain). Further, the inventors have found that tenderness has depth and breadth, a muscle induration has hardness and magnitude, and there is a classification of the cause of pain into tenderness and an induration. Further, currently, treatment is conducted unthinkingly with respect to a portion in which a patient subjectively complains of strongest pain or the like. The inventors have found that there is a shift between a portion in which the patient complains of pain subjectively and a portion which causes pain objectively. For example, in the case where a patient complains of pain over the entire front surface of a knee, an induration is present at the back of the knee, and in the case of palsy pain from a front arm inside elbow to a fifth finger, tenderness is present in a neck upper part of an affected side. Further, the inventors have found that tenderness is present on an affected side of fourth and fifth lumber spines in the case of pain, palsy, chill, etc. on the front surface of a "crural area", and the like. Thus, the precision of alleviating pain has further increased. When the tender area spreading in a geographical shape and/or the entire induration was treated by a treatment method in accordance with the classification of the cause of pain, the neurological disorder, deterioration, or damage, and muscle induration were recovered effectively and quickly, and the accompanying pain and other various conditions were ameliorated dramatically.

In other words, the present invention includes the following.

1. A skin patch for treating pain, in which a sheet-shaped patch A having a size of 5 to 15 cm on a side, in which one of a plurality of fine metal grains each having a particle diameter of 0.1 to 1.8 mm and a plurality of crushed stones each having a particle diameter of 0.5 to 3 mm adheres to a surface, is attached to at least one of a tender area and an induration, which are confirmed by pressing, so as to fully cover at least one of the tender area and the induration.

2. A skin patch for treating pain, in which a plurality of sheet-shaped patches B having a maximum length of 1.5 to 3 cm, in which one of one or two metal grains each having a particle diameter of 3 to 10 mm and a plurality of crushed stones each having a particle diameter of 1 to 5 mm adhere to a surface, are attached to at least one of a tender area and an induration, which are confirmed by pressing, so as to fully cover at least one of the tender area and the induration, the patches being overlapped with and adjacent to each other.

3. A skin patch for treating pain according to the item 1, in which the patch A, in which one of the plurality of fine metal grains and the plurality of crushed stones adheres to the surface, is attached to at least one of the tender area and the induration, which are confirmed by pressing, so as to fully cover at least one of the tender area and the induration, and then, at least one sheet-shaped patch B, in which one of one or two metal grains each having a particle diameter of 3 to 10 mm and a plurality of crushed stones each having a particle diameter of 1 to 5 mm adhere to a surface and a maximum length is 1.5 to 3 cm, is attached from above the patch A.

4. A skin patch for treating pain according to the item 3, including a kit including the patch A and the patch B.

5. A skin patch for treating pain according to any one of the items 1 to 4, in which at least one of a tender area and an induration spreading geographically is confirmed by pressing with one of a pressing bar and a finger.

6. A skin patch for treating pain according to the item 5, in which both ends of the pressing bar each have one of a ball shape, a semi-spherical shape, and a spherical shape, and the pressing bar has a diameter of 4 to 8 mm, a length of 20 to 25 cm, and a weight of 85 g to 100 g.

7. A skin patch for treating pain according to any one of the items 1 to 6, in which the plurality of fine metal grains of the patch A each have a particle diameter of 0.1 to 1.8 mm, an interval between the grains is 0 to 12 mm, and the fine metal grains are arranged in a lattice, or the crushed stones of the patch A each have a particle diameter 0.5 to 3 mm and the patch A is encrusted with the crushed stones at random.

8. A skin patch for treating pain according to any one of the items 2 to 6, in which the metal grains of the patch B each have a particle diameter of 3 to 10 mm and a height of 1 to 5 mm.

9. A skin patch for treating pain according to any one of the items 2 to 6, in which the crushed stones of the patch B each have a particle diameter of 1 to 5 mm, and the patch B is encrusted with the crushed stones at random.

10. A skin patch for treating pain according to any one of the items 1 to 6, including a kit including crushed stones each having a particle diameter of 0.5 to 3 mm, crushed stones each having a particle diameter of 1 to 5 mm, a sheet-shaped member having a size of 5 to 15 cm on a side, to which an adhesive agent is applied, and a sheet-shaped member having a maximum length of 1.5 to 3 cm, to which an adhesive agent is applied.

11. A use for treating pain of the sheet-shaped patch A having a size of 5 to 15 cm on a side, in which one of a plurality of fine metal grains each having a particle diameter of 0.1 to 1.8 mm and a plurality of crushed stones each having a particle diameter of 0.5 to 3 mm adheres to a surface, according to any one of the items 1 to 10, the use including: (1) confirming a tender area by pressing with one of a pressing bar and a finger; and (2) attaching the sheet-shaped patch A so as to fully cover the confirmed tender area.

12. A use for treating pain of a sheet-shaped patch B having a maximum length of 1.5 to 3 cm, in which one of one or two metal grains each having a particle diameter of 3 to 10 mm and a plurality of crushed stones each having a particle diameter of 1 to 5 mm adheres to a surface, the use including: (1) confirming at least one of a tender area and an induration by pressing with one of a pressing bar and a finger; and (2) attaching a plurality of the sheet-shaped patches B so as to fully cover at least one of the confirmed tender area and induration.

13. A use for treating pain of a combination of the patches A and B, including: (1) confirming at least one of a tender area and an induration by pressing with one of a pressing bar and a finger; (2) attaching a sheet-shaped patch A having a size of 5 to 15 cm on a side, in which one of a plurality of fine metal grains each having a particle diameter of 0.1 to 1.8 mm and a plurality of crushed stones each having a particle diameter of 0.5 to 3 mm adheres to a surface, so as to fully cover at least one of the confirmed tender area and induration; and (3) attaching at least one sheet-shaped patch B having a maximum length of 1.5 to 3 cm, in which one of one or two metal grains each having a particle diameter of 3 to 10 mm and a plurality of crushed stones each having a particle diameter of 1 to 5 mm adheres to a surface, to a part of pain and an induration from above the patch A.

The inventors of the present invention have found that the geographical tender area and/or an induration is present on a skin by pressing the skin with a pressing bar or fingers (first to fourth fingers), and there is a classification of the cause of pain into tenderness, an induration, and both of the tenderness and an induration.

Further, a tender area up to a boundary thereof and/or an entire induration is compressed with metallic grains or crushed stones by a treatment method in accordance with the classification of the cause of pain (mainly a therapeutic patch A for tenderness, mainly a therapeutic patch B for an induration, and a combination of the therapeutic patches A and B for the presence of both of the tenderness and the induration). Further, in a patient suffering from a knee pain, the following therapeutic effect was recognized: a visual analyze scale (VAS) changed from an average of 65.8±8.4 before the treatment to an average of 14.3±12.0 after the treatment of 3 days with a risk rate of less than 1%. Here, the risk rate of 1% means the reliability that the treatment can be conducted at a probability of 99%.

Further, similar therapeutic effects were recognized even in pain at other sites of a body (Table 2).

Thus, even in the case where there is a shift between a portion in which a patient complains of pain subjectively and a portion which causes pain objectively, a neurological disorder, deterioration, or damage can be recovered effectively and quickly (that is, a tender part is pressed to eliminate pain completely), and a muscle induration can be flexed to recover the muscle to a soft one, and the accompanying pain and other various conditions can be eliminated and ameliorated.

DETAILED DESCRIPTION OF THE PREFERRED EMBODIMENTS

Figure 1:
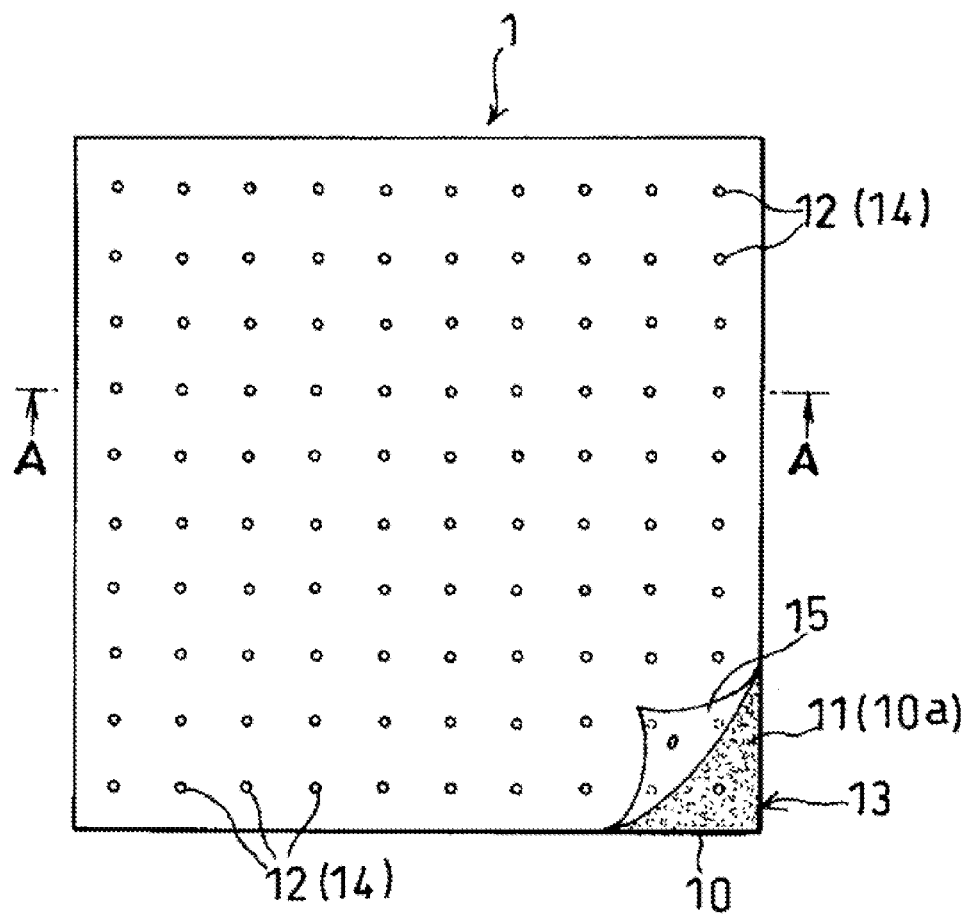
FIG. 1 is a plan view of a patch A according to the present invention.

Pain in the present invention refers to pain which a patient feels subjectively, i.e., subjective pain, occurring in any part of a body. The pain in the present invention refers to pain caused by emotional internal factors such as extreme stress and overfatigue caused by pressure of work, pain from a visceral disease typified by cancer, and pain caused by external factors such as sprain, bruise, bone fracture, after care of bone fracture, and postsurgical adhesion.

To be more specific, the pain in the present invention can be applied to any pain such as pain in knee, general nerve pain, sports disorders and external injury, shoulder joint and peripheral pain, lumbar hernia, sprain of an ankle joint, chronic headache, migraine, neck and shoulder peripheral pain, inner elbow outside pain, coxalgia, and intercostal neuralgia.

The pain in the present invention includes any one of the cases of chronic disorders, acute disorders, and chronic and acute disorders each caused irrespective of whether a patient is old or young, male or female, fat or slim, and the like.

The chronic disorders each refer to a state in which pain stays for 6 months or more continuously or intermittently after the emergence of the pain (International Association for the Study of Chronic Pain). Sensory conditions such as pain, heaviness, stiffness, fullness, stitch, palsy, and uncomfortable feeling are phenomena caused by the shortage of the amount of blood flow, depending upon the degree of neurological deterioration (disconnection of neural transmission, etc.), which also causes chronic disorders.

The acute disorders refer to disorders in which pain occurs rapidly in a short period of time.

The chronic and acute disorders refer to disorders in which the degree of pain is small and negligible although the pain stays continuously or intermittently, but stronger pain occurs rapidly after a certain bodily movement.

Treatment in the present invention refers to finding a tender area boundary and an induration (deteriorated muscle) that are the causes of pain found by the inventors of the present invention, and attaching a therapeutic patch for treating pain of the present invention thereto.

A minus bioelectric potential is always present on the skin surface of a healthy human body. However, when a neurological disorder, deterioration, or damage occurs, the bioelectric potential of a part in which the neurological disorder, deterioration, or damage occurs is converted from a minus state to a plus state. It is considered that a neural function is simultaneously deteriorated, leading to tenderness and an induration that are the causes of pain, and pain, heaviness, palsy, stiffness, stitch, uncomfortable feeling, etc. occur depending upon the degree of the degradation in neural function.

Therefore, when metallic grains containing minerals are attached to that part from above the skin, followed by compressing, mineral ions can be transmitted to the skin and permeated therethrough to convert the bioelectric potential to a normal minus state. This is considered to recover a neurological disorder, deterioration, or damage to ameliorate pain and other various conditions (Japanese Patent Application Laid-open Nos. 2002-209973 and Sho 61-15703).

Further, similar effects are obtained even with crushed stones instead of the metallic grains in the present invention.

Figure 7:
FIG. 7 shows a pressing bar.

Pressing in the present invention refers to pressing a site of pain in which a patient complains of pain subjectively with a bar shown in FIG. 7 or fingers (first to fourth fingers). The degree of a pressing force is adjusted to such a degree that pain can be recognized while checking with the patient. Further, it is preferred to press the site of pain to such a degree as not to put a burden on an affected part while considering the condition.

It has been found that tenderness and/or an induration is present without fail in a site of pain in which a patient complains of pain subjectively. In searching for tenderness, however, it is necessary to use a pressing bar for pressing a site with a strong pressure, which cannot be pressed with a finger force due to the fullness of a muscle, or a small place where a finger is unlike to enter, or for determining a tenderness boundary clearly. Further, in order to determine the hardness or magnitude of an induration, the first to fourth fingers may be used.

The pressing bar in the present invention refers to one with both ends in a ball shape, a semi-spherical shape, or a spherical shape having a diameter of 4 to 8 mm, having a length of 20 to 25 cm, a circumference of 42 mm, and a weight of 85 to 100 g. FIG. 7 shows one optimum example. The optimum pressing bar has a weight to some degree, without which deep tenderness cannot be found, and has a length that is neither so long nor so short that any problem in operation arises. The optimum pressing bar also has a portion to be held by a hand that is similarly neither so thick nor so thin.

The pressing bar preferably has a leading end with a diameter of 5 mm, a trailing end with a diameter of 7 mm, a length of 23 cm, and a weight of 85 g.

The reason why the pressing bar preferably has ball-shaped, semi-spherical, or spherical ends is that such pressing bar hardly damages a skin and the like, allows a pressing force to be concentrated on one point, and is likely to determine the cause of pain and the depth of tenderness.

The reason why the pressing bar preferably has a diameter of 4 to 8 mm is that such pressing bar can target a site of tenderness precisely. In general, in the case of searching for tenderness, a trailing end of 7 mm is preferred. However, in order to target a slight gap of overlapping metal particles and check a deeper site, a trailing end of about 5 mm is preferred.

A pressing bar which is too long or too short is difficult to use. A pressing bar which is too light or too heavy is also difficult to use. Although the pressing bar shown in FIG. 7 is made of metal, a pressing bar made of a material other than metal may also be used.

Further, when a muscle hardness meter is attached to the pressing bar, an objective index can be displayed to a patient along with the alleviation of pain.

Such pressing bar has not been used by anybody except for the inventors of the present invention et al.

The site of pain in the present invention refers to a site in which a patient subjectively complains of pain and other various conditions. The site of pain has tenderness and/or an induration. However, this is not always the case. For example, in the case where there is pain on an entire knee front surface, an induration is present at the back of the knee as a classification of the cause of pain. In the case of palsy and pain from malleolus medialis to the fifth finger, tenderness is present in a neck upper part of an affected side as the cause of pain. In the case of palsy and pain from lateral malleolus to the thumb, tenderness is present in the periphery of a seventh cervical spine. In the case of pain, palsy, chill, or the like on a crural area front surface, tenderness is present on the periphery of an affected side of fourth and fifth lumber spines as the cause of pain. The cause of pain may be present in an upper part of a site in which a patient complains of pain. Due to the above-mentioned and other findings, the precision of alleviating pain has increased further. By conducting medical care with respect to disordered sites of 15,000 or more cases, it was confirmed that there was a shift between a site of pain (site of subjective pain) and a site that causes pain.

The cause of pain in the present invention refers to an inductive and objective site of pain. Currently, a detailed cause of pain has not been clarified (International Association for the Study of Chronic Pain). However, the cause of pain according to the present invention is classified by pressing with a pressing bar or fingers (first to fourth fingers) into tenderness (method of clearly searching for the cause of pain by extracting pain inductively by pressing an affected part) and an induration (method of clearly searching for the cause of pain objectively, the pain being ascribed to an induration caused by the deterioration of a muscle or the like). The inventors of the present invention found the classification. An induration can be recognized based on the sense of fingers because a muscle is stiff in an affected site when the affected part is pressed. The pain caused by other factors is classified as tenderness.

One of the classification of the cause of pain of the present invention is tenderness. The tenderness if further classified into the following stages when a patient feels pain inductively using a pressing bar: 1. a patient feels strong pain by light pressing (to such a degree that the pressing bar rubs against or is rolled over an affected part); 2. a patient feels pain by some compression (to such a degree that concaves can be formed by pressing with a force that does not break a balloon); 3. a patient feels pain by strong pressing (to such a degree that a balloon is broken), and 4. a patient does not feel any pain even by strong pressing. Further, another is an induration, through which the cause of pain of a patient can be objectively known. According to this method, the hardness or magnitude of a muscle induration that becomes stiff is distinguished based on the sense (touch) of the fingers (first to fourth fingers) by palpation. These causes are roughly classified into the tenderness and the induration.

The tenderness in the present invention refers to a sensory nerve sense of pain disorder of autonomous nerves, etc. It is considered that pain is caused by a sensory nerve disorder.

The tender area in the present invention refers to an entire tender including a boundary thereof.

The tender area is easily understood by considering a bruise state. The bruise differs in tender area and boundary thereof depending upon the shape of a striking object such as a ball or a bamboo sword. The depth of damage also differs depending upon the striking strength. In the process of healing of bruise, subjective symptom is also alleviated in proportion with the alleviation of tenderness. That is, it is considered that the reduction or elimination of tenderness is the alleviation or elimination of subjective pain, and tenderness (neural disorder) is the cause of pain. The tenderness is considered to cause pain through a sensory nerve disorder, and hence, allowing these nerves to recover is the elimination of tenderness, which is equal to the elimination of pain (subjective pain), which leads to healing without recurrence.

Similarly, the same applies to tenderness caused by disorders other than bruise. Further, considering the recurrence aspect, as long as such tenderness remains, no complete healing is obtained, and pain is considered to recur even if pain is eliminated temporarily.

The induration of the present invention is considered to be caused when a somatic disorder causes the deterioration of nerves controlling a muscle or the like, and consequently, blood cannot be supplied to the muscle. That is, the induration refers to a state in which a muscle is deteriorated and further hardened. In general, a healthy muscle is rich in extensibility and has flexibility, whereas a deteriorated muscle is hardened, and hence, loses extensibility and decreases in flexibility. Thus, the deteriorated muscle cannot extend to a range in which a healthy muscle can originally extend, and the difference therebetween is exhibited as pain. Further, the hardness of induration of a muscular substance differs depending upon the age. Although the induration of a muscular substance is hard, thick, and large like a stratum at a later age, it was confirmed that the induration of a muscular substance is decompressed by several treatments. Further, rupture of Achilles' tendon, rupture of anterior cruciate ligaments of the knee, muscle strain, Charley, convulsion, stiff shoulder due to age, etc. are phenomena that start from the deterioration of a muscular substance, tendon, and ligament and occur when they are hardened.

Figure 8:
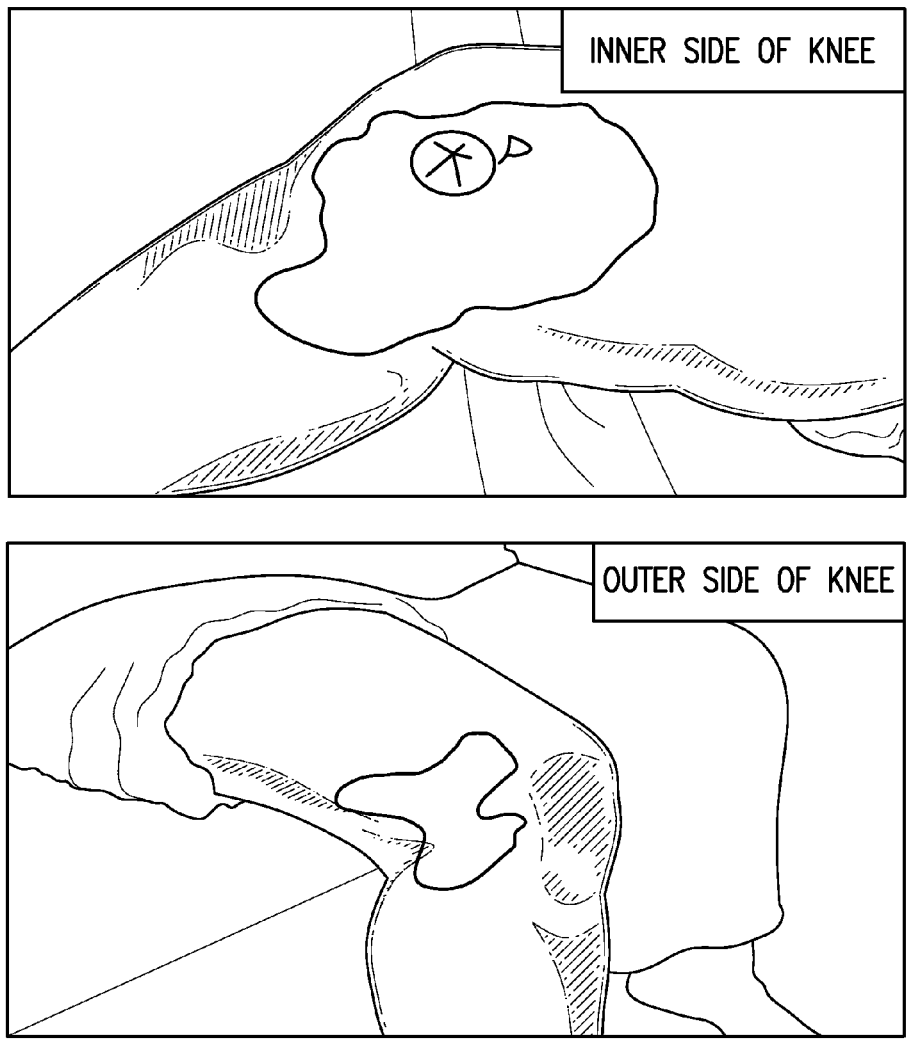
FIG. 8 shows pictures showing boundaries and a part of pain in which a patient complains of pain particularly, the pictures showing an inside knee and an outside knee, respectively.
Figure 9A:
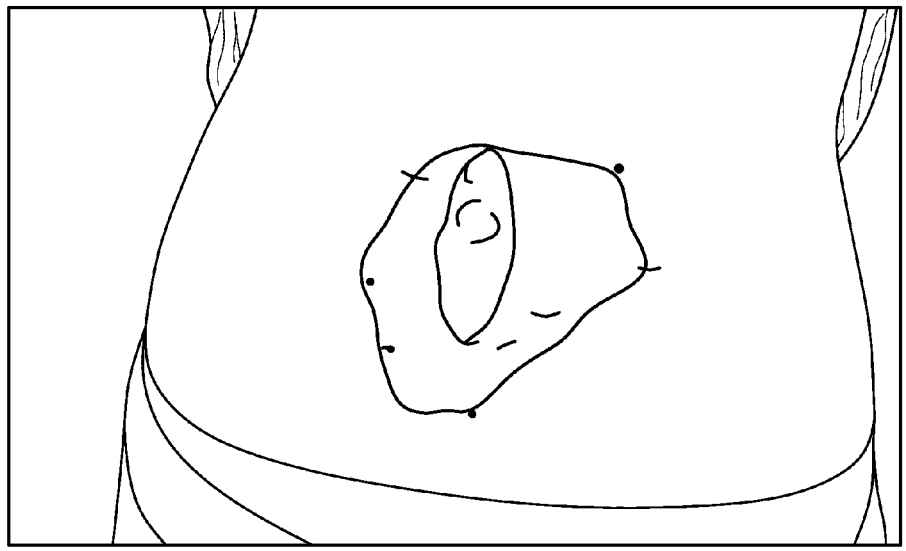
FIG. 9 show pictures showing a boundary and an induration.
Figure 9B:
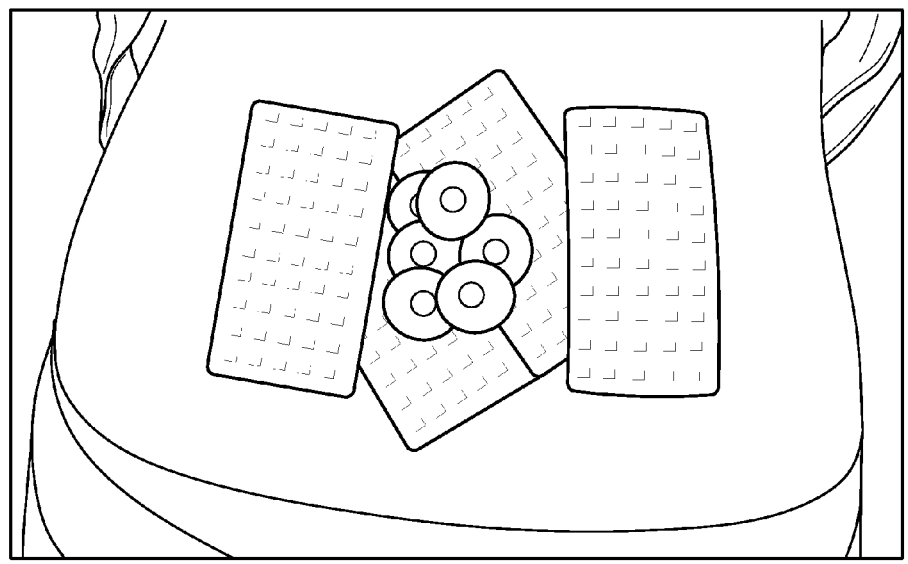

The boundary of the present invention refers to a border between a portion in which a patient feels pain when the pain is derived inductively by pressing and a portion in which the patient has no pain. By clarifying the boundary of a tender area, subjective pain which a patient complains of can be known as objective information. Further, the presence of such objective pain has been found by the inventors of the present invention, and currently is a unique finding. FIG. 8 shows an example confirming boundaries and a part of pain in which a patient feels particularly strong pain. Marks were put on the body with a pen or the like having no problem in direct use for the body. Further, the part of pain in which the patient feels particularly strong pain was marked with a circle with a character "大".. FIG. 9 also show examples of confirming a boundary and induration. A large surrounded region corresponds to the boundary, and a small surrounded portion corresponds to the induration. FIG. 9A shows the state before the therapeutic patch of the present invention is attached, and FIG. 9B shows the state after the therapeutic patch of the present invention is attached.

Regarding the neurological deterioration in the present invention, when nerves are considered as an electric transmission path and the case where the supply amount of electricity is 100 is considered as a healthy state, the state in which the supply amount of electricity decreases 80, 60, 50, and 40 is considered the neurological deterioration. The degree of deterioration refers to the state in which the neurological deterioration is stabilized. In proportion with this, the shortage of amount of blood flow occurs, which is considered as a cause for forming an induration and tenderness that also cause chronic pain disorders.

Figure 2:
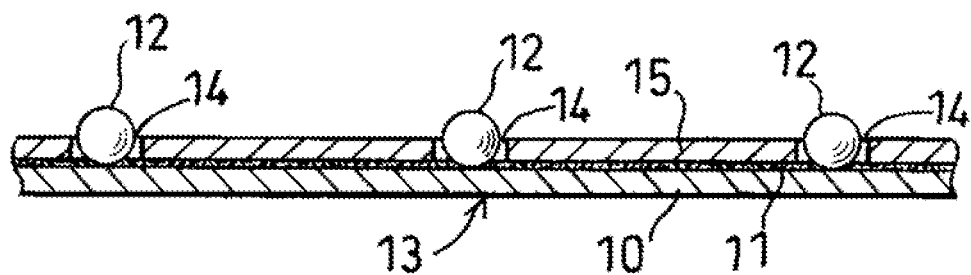
FIG. 2 is an enlarged cross-sectional view taken along the line A-A of FIG. 1.

A patch A of the present invention, which is shown as patch 1 in FIG. 1, includes a pressure-sensitive adhesive sheet 13 in which a plurality of metal grains 12 are arranged at a predetermined interval on a pressure-sensitive adhesive layer 11 that is one surface of a seat member 10, and a peeling sheet 15 peelable from the pressure-sensitive adhesive layer 11 which is provided with small holes 14 at positions corresponding to the respective metal grains 12 and in which the respective metal grains 12 protrude from the small holes 14 (FIGS. 1 and 2)

The sheet member 10 is formed of paper having strength and flexibility, nonwoven fabric, cloth, or a resin sheet having plasticity. The sheet member 10 has a thickness of 1 mm or less. The pressure-sensitive adhesive layer 11 is provided on one surface 10a of the sheet member 10 by coating with a pressure-sensitive adhesive. When a resin sheet is used, the plurality of metal grains 12 may be attached and fixed to the sheet member previously, and an adhesive may be applied to the surface to form the pressure-sensitive adhesive layer 11.

The sheet member 10 may have any size as long as the sheet member 10 can be attached to a tender area of the surface of a skin and/or an entire induration. For example, a square shape or a rectangular shape with a side of 5 to 15 cm, economically, 8 to 10 cm, is preferred considering the application to each site of a body and a cost. In use, the sheet member 10 can be cut to a size corresponding to an affected part. The sheet member 10 preferably has an inconspicuous color matched with the skin color, considering the privacy of a patient and the like.

The peeling sheet 15 is formed of paper, a resin sheet, or the like having flexuosity, flexibility, and strength. One surface of the peeling sheet 15 is treated so as to be peeled easily from the pressure-sensitive adhesive layer 11. Further, the peeling sheet 15 is provided with a plurality of small holes 14 so that the small holes correspond to the arranged positions of the plurality of metal grains 12.

The minute metal particles (metal grains 12 of FIG. 1) are made of metal, and examples of the metal include iron, copper, chromium, gold, silver, lead, tin, aluminum, stainless steel, germanium, and titanium. Metal with any composition may be used as long as mineral ions generated from minute metal particles can convert the bioelectric potential of a skin.

The diameter of each of the metal grains 12 is about 0.1 to 1.8 mm. When the diameter is 0.1 mm or less, the metal grains are too small to provide a sufficient compression action on a skin, and sufficient effects cannot be expected. Further, when the diameter is 1.8 mm or more, the metal grains are too large and may break into a skin of a human body to cause uncomfortableness. To be specific, when the metal grains are large, it is difficult for an examiner to attach a therapeutic patch to a small part such as a finger of a hand or a foot, a heel, a sole, or the like, and the patch influences an operation conducted by a patient to become an obstacle and the metal grains are likely to peel. Further, when the patch is attached to a sole, an uncomfortable feeling continues to cause stress due to the applied weight.

The metal grains each desirably have a spherical shape, but the shape is not particularly limited and a semispherical shape, a cylindrical shape, a polygonal pyramid shape, or the like can be used.

It should be noted that the amount of ions to be generated differs depending on the size and shape of the metal grains. Information was gathered from 15,000 or more patients, and the best shape and size were obtained.

The size and shape of the metal grains may preferably be such that mineral ions to be generated from the arrangement of the minute grains can reach a deep part uniformly.

The arrangement of a plurality of minute metal grains refers to one that has a lattice shape and is swollen in which the interval of the plurality of minute metal grains is 0 to 12 mm. The interval of the plurality of minute metal grains is preferably 4 to 8 mm.

As the interval of the metal grains is smaller, the contact surface between the metal grains and a skin is larger, which maximizes the effects of mineral ions. When the metal grains are attached to a skin surface in a special manner, the depth of tenderness or the hardness and size of an induration, etc., and the presence of a gap of only several millimeters between the metal particles influence the elimination of pain. Therefore, a gap is preferably as small as possible. This is not always the case when there is no hardness of an induration or an induration is small due to younger age or the like, or when tenderness has no depth and is large and shallow.

If the interval is 0 mm, the adjacent minute metal grains are in contact with each other, which can bring about pressing effects of fingers efficiently and generate mineral ions efficiently. However, in this case, adhesive effects may be lost and the metal grains may be floated. Therefore, the interval is preferably 4 to 8 mm. Further, the distance interval depends upon the magnitude and hardness of an induration, the depth and shallowness of tenderness, and the like.

Further, the following was confirmed from the results of experiments. When the interval was 12 mm or less, subjective pain was eliminated. When the interval was 12 mm or more, the interval of adjacent metal grains was too large, and hence, mineral ions were not emitted uniformly, with the result that pain was not eliminated completely.

The patch A of the present invention may be encrusted with crushed stones and used. The crushed stones are suitably prepared from a material containing minerals such as sedimentary rock (clast (sandstone, conglomerate, mudstone, shale, etc.), volcaniclastic rock (tuff, etc.), biogenic rock (chert, limestone, etc.)). When crushed stones are used for the patch A, stone crushed to a diameter of 0.5 to 3 mm, preferably about 0.9 to 2.5 mm, can be used. Regarding the arrangement of the crushed stones on a sheet, it suffices that the sheet is randomly encrusted with the crushed stones. Needless to say, the crushed stones may be arranged in the same way as the above-mentioned minute metal grains by adjusting the diameter of the crushed stones.

A patch B of the present invention includes a pressure-sensitive adhesive sheet 23 in which metal grains 22 are provided on a pressure-sensitive adhesive layer 21 that is one surface of a sheet member 20 and a peeling sheet 24 peelable from the pressure sensitive adhesive layer 21 (FIGS. 3, 4, 5, and 6).

The sheet member 20 is formed of the same material as that for the sheet member 10 of FIG. 1.

The sheet member 20 may have any size as long as the sheet member 20 can be attached to a skin of a human body. However, when the size is too small, the contact surface of the sheet member 20 with respect to the skin becomes small and the sheet member 20 is liable to peel. Too large a size causes a cost problem. The sheet member 20 is a sheet having a largest length of about 1.5 to 3 cm, preferably 2 to 3 cm, and preferably has a circular shape so that an end is unlikely to peel.

The color is preferably one that is matched with the skin in terms of the privacy of a patient or the like.

The peeling sheet 24 is formed of the same material as that for the peeling sheet 15 of FIG. 1.

Figure 3:
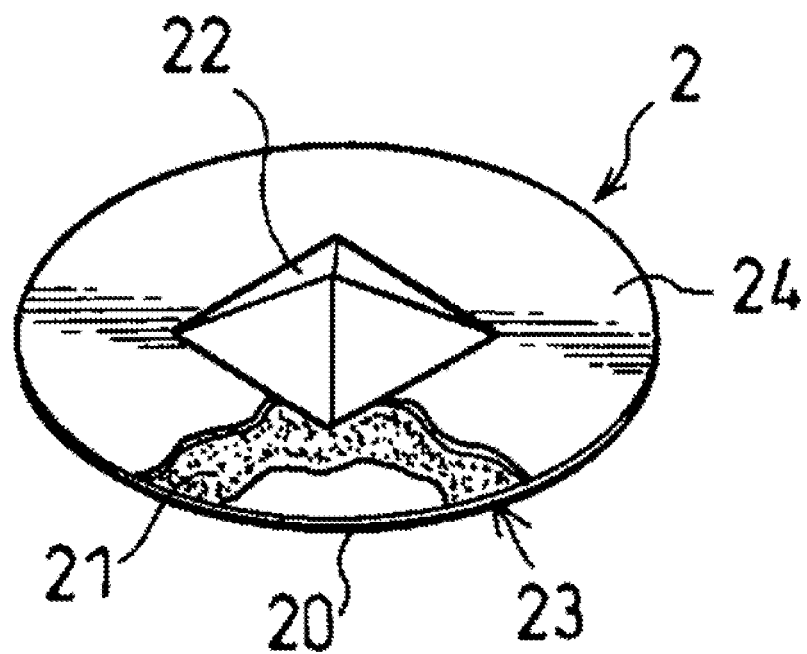
FIG. 3 is a schematic perspective view illustrating an example of a patch B according to the present invention.
Figure 4:
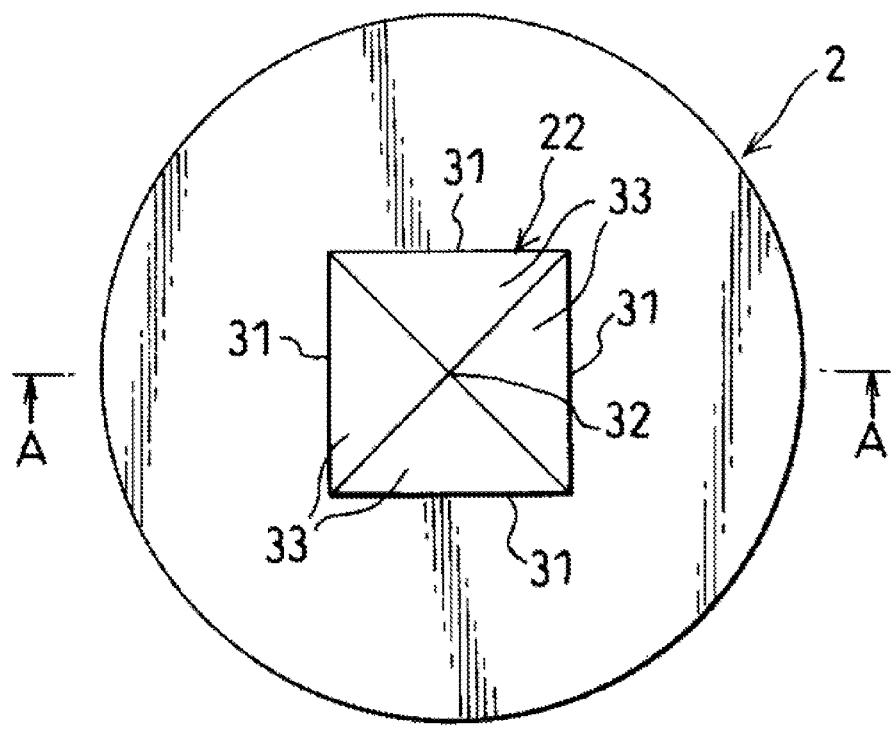
FIG. 4 is a plan view of the patch B according to the present invention.
Figure 5:
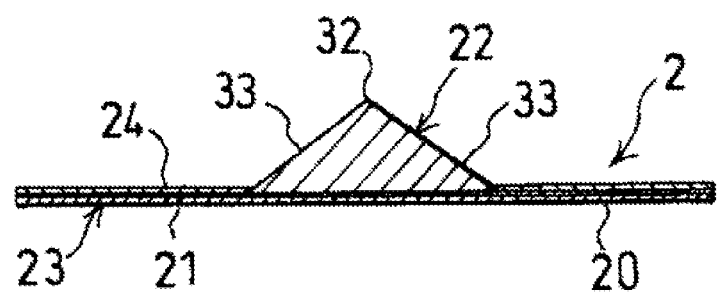
FIG. 5 is a cross-sectional view taken along the line A-A of FIG. 4.

The metal grains (metal grains 22 of FIGS. 3, 4, 5 and 6, wherein metal grains 22 in FIGS. 4 and 5 are shown to include features 32 and 33) of the patch B are formed of the same material as that for the fine metal grains (metal grains 12 of FIGS. 1 and 2), wherein patch B is shown as patch 2 in FIGS. 3, 4, 5 and 6.

The diameter of the metal grains is 3 to 10 mm, preferably 5 to 10 mm, and the height thereof is about 1 to 5 mm.

FIG. 3 illustrates a quadrilateral shape. One side 31 of a bottom surface thereof has a size of 5 to 10 mm, and the height thereof is 1 to 5 nm. However, the shape is not particularly limited, and may be a spherical shape, a semispherical shape, a cylindrical shape, a polygonal pyramid shape, a disc shape, an oval disc shape, a pyramid shape, a sword point shape, a needle point shape, or the like, instead of the quadrilateral shape. In the case where the metal grains have magnetism, a pyramid shape, a sword point shape, or a needle point shape is preferred so as to keep the shape. If the metal grains have no magnetism, there is no particular limit to the shape.

The metal grains may preferably be such that ions generated from the metal grains can reach a deep part uniformly.

One or two metal grains are placed at the center of the sheet in the patch B.

The patch B of the present invention may be encrusted with crushed stones and used. The crushed stones are suitably prepared from a material containing minerals such as sedimentary rock (clast (sandstone, conglomerate, mudstone, shale, etc.), volcaniclastic rock (tuff, etc.), biogenic rock (chert, limestone, etc.)). When crushed stones are used for the therapeutic patch B, stone crushed to a diameter of 1 to 5 mm, preferably about 1.5 to 3 mm, can be used. Regarding the arrangement of the crushed stones on a sheet, it suffices that the sheet is randomly encrusted with the crushed stones. Needless to say, about 1 to 6 crushed stones may be arranged in the same way as the above-mentioned metal grains by adjusting the diameter of the crushed stones.

A kit including the patch A and the patch B of the present invention includes the patch A and the patch B as defined above. The kit can include other members used for treating pain, such as a pressing bar and a sheet member for replacement, in addition to the patch A and the patch B.

A patch using crushed stones is produced as follows. First, stone is crushed to a diameter of 1 to 5 mm. Then, an adhesive agent is applied to a rectangular or circular sheet member 10 or 20, and the resultant sheet member 10 or 20 is covered with a peeling sheet 15 or 24 that is peelable. The peeling sheet 15 or 24 has a tear line, and only a center part can be peeled. The crushed stones are attached uniformly to the center part from which the peeling sheet 15 or 24 has been peeled. Alternatively, a circular or rectangular sheet 10 or 20 coated with an adhesive agent is prepared, and crushed stones are attached thereto uniformly. After that, the sheet member 10 or 20 is covered with the peeling sheet 15 or 24.

Preferably, stone has no magnetism. If stone has magnetism, stones are bound by each other, and a sheet may curl up.

A kit including crushed stones and a sheet member coated with an adhesive agent includes crushed stones and a sheet member coated with an adhesive agent. The kit can include other members used for treating pain, such as the peeling sheet 10 or 20 and a pressing bar, in addition to the crushed stones and the sheet member coated with an adhesive agent. Further, the diameter of the crushed stones is discriminated as in the above-mentioned patches A and B, smaller (0.5 to 3 mm) and larger (1.5 to 3 mm) ones may be divided to provide a kit including a sheet for the patch A and a sheet for the patch B.

The case of using the therapeutic patch A of the present invention corresponds to the case where tenderness (nerves) are large and shallow and damage or functional deterioration occurs. The therapeutic patch A is preferably used for acute disorders, acute external injury, injury disorders, neuralgia, and the like. The therapeutic patch A is more preferably used for external injury caused by sprain or bruise, intercostal neuralgia, sciatica, heel pain, pain in knee, lumbar pain, stiff shoulder, and the like.

According to a method of using the therapeutic patch A, first, a tender area and a boundary thereof are confirmed by pressing with a bar or fingers (mainly, a thumb) (See FIG. 8).

Then, the peeling sheet 15 of the therapeutic patch A is peeled, and the sheet member 10 is attached up to the boundary of the entire tender area so that the metal grains 12 or crushed stones come into contact with the skin surface.

At this time, the therapeutic patch A is appropriately cut to a size in accordance with the boundary for use.

Figure 10:
FIG. 10 shows a method of using the patch A.

FIG. 10 shows a method of using the therapeutic patch A.

The case of using the therapeutic patch B of the present invention corresponds to the case where a portion in which tenderness is deep (nerve abnormality depth) or an induration has hardness and is large. In these cases, a plurality of therapeutic patches B are used while being overlapped without any gap. It has been confirmed that even a slight gap of about 5 mm may cause pain. The therapeutic patch B is preferably used for chronic disorders, etc., and is preferably used for serious cases such as chronic sprain, chronic pain caused by bruise or the like, chronic intercostal neuralgia and cingulum, chronic sciatica, chronic (heel pain, pain in knee, lumbar pain, stiff shoulder, neck pain, stiff shoulder due to age, omalgia, headache, fatigue of the eye, pain in a deep part, etc.) cervical part, lumbar hernia, or the like.

According to a method of using the therapeutic patch B, first, a tender area and a boundary thereof and/or an induration that is the cause of pain is confirmed by pressing with a bar or fingers (first to fourth fingers) (see FIGS. 8 and 9).

Then, the peeling sheet 24 of the therapeutic patch B is peeled, and the sheet member 20 is attached so that the metal grains 22 or crushed stones come into contact with the skin surface.

Figure 6:
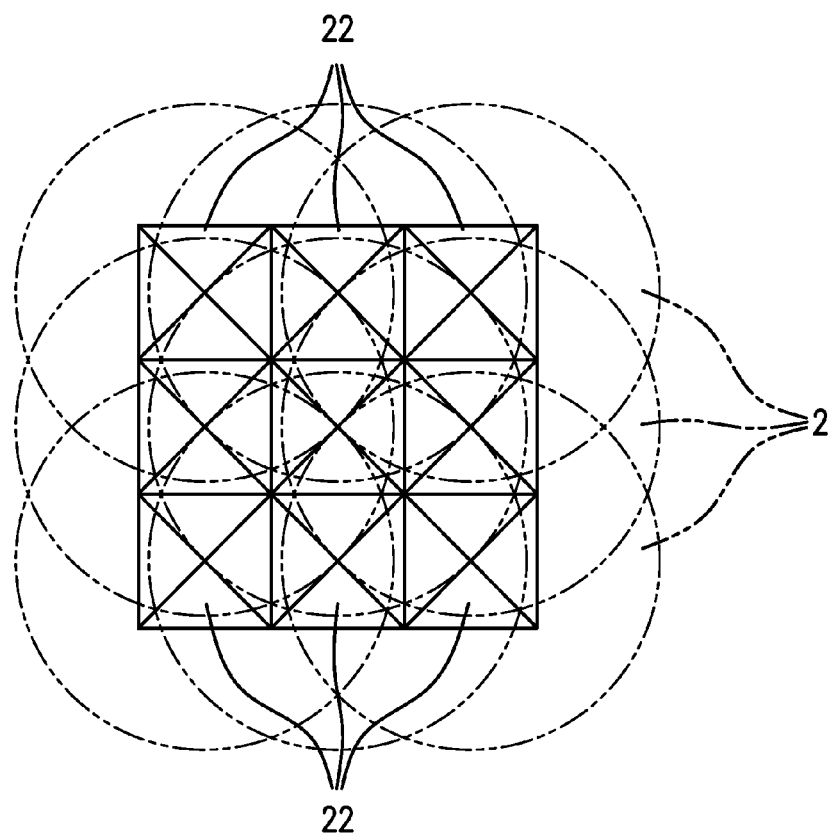
FIG. 6 is an in-use view illustrating an attached plurality of patches B according to the present invention.

At this time, a plurality of the therapeutic patches B are overlapped and attached to the entire tender part up to a boundary thereof or an induration so as to cover the entire induration, in such a manner that the adjacent metal grains 22 or crushed stones are brought into contact with the entire tender area up to the boundary or the induration as much as possible (see FIG. 6). In this case, the metal grains 22 or crushed stones may not come into direct contact with a skin. The adjacent metal grains 22 or crushed stones may not come into direct contact with the surface of a skin. Even when the adjacent metal grains 22 or crushed stones are not in direct contact with the surface of a skin, mineral ions from the respective metal grains 22 or crushed stones pass through the sheet member 20 (the passage of mineral ions through the member 20 is found by the inventors of the present invention, and mineral has been directly attached to a skin. Further, the development of this attachment method has enabled the complete pain elimination effects). Therefore, the mineral ions can act on the surface of a skin, and even when tenderness is in a deep part and/or there is a hard and large induration, the tenderness and/or induration can be flexed and recovered.

Figure 11:
FIG. 11 shows a method of using the patch B.

FIG. 11 shows the method of using the therapeutic patch B.

The case of using a combination of the therapeutic patches A and B of the present invention refers to the case where tenderness (neural disorder) is large and shallow, and also the case where there is a hard induration in the tender area. The combination of the therapeutic patches A and B of the present invention is preferably used for pain of overall internal organs, chronic and acute disorders, chronic disorders, acute external injury, injury disorders, and the like. The combination is more preferably used for the case where tenderness such as external injury caused by sprain or bruise, sciatica, heel pain, pain in knee, lumbar pain, stiff shoulder, or the like is present in a wide range, and a hard and large induration and neural disorder are present in a deep part in the range. Pain may remain between metal grains when the therapeutic patch A is used, and hence, the therapeutic patch B is attached to the interval. As the interval of the metal grains is smaller, the contact surface between the metal grains and a skin is larger, and hence, the effects of mineral ions can be exhibited to the most.

According to a method of using the combination of the therapeutic patches A and B, first, a tender area and a boundary thereof and/or an induration that is the cause of pain is confirmed by pressing with a bar or fingers (first to fourth fingers) (see FIGS. 8 and 9). Then, the peeling sheet 15 of the therapeutic patch A is peeled, and the sheet member 10 is attached up to the boundary of the entire tender area and the entire induration so that the metal grains 12 or crushed stones come into contact with the skin surface.

At this time, the therapeutic patch A is appropriately attached to a tender area up to a boundary, and in the case where the tender area is large, some therapeutic patches A are used and the remaining can be cut to be used for other areas. The most important thing is that the therapeutic patch A is attached to the entire tender area up to a boundary thereof. Further, in the case where there is a tender part or an induration part in which a patient complains of particularly strong pain, which has been checked by pressing, the therapeutic patch A is attached thereto, and the therapeutic patch B is overlapped with the therapeutic patch A (see FIGS. 8 and 9). Thus, pain can be removed more precisely and more reliably.

In this case, the metal grains 22 or crushed stones may not be brought into direct contact with a skin. Even when the adjacent metal grains 22 or crushed stones are not brought into direct contact with the surface of the skin, the sheet member 20 of the adjacent therapeutic patch B allows mineral ions from the respective metal grains 22 or crushed stones to pass through the sheet member 20. Therefore, the mineral ions can act on the surface of the skin, and even in the case where there is tenderness and/or an induration in a deep part, the induration can be flexed and a neural disorder in a deep part can also be recovered.

Figure 12:
FIG. 12 shows a method of using a combination of the patches A and B.

Similar effects are obtained, even when compared with the case where only a plurality of therapeutic patches B are attached so as to be overlapped with each other, and the cost can be saved about 5 to 8 times. In the case where tenderness (neural disorder) is large and shallow, a considerable difference in cost is caused only with the therapeutic patch B. Therefore, a combination of the therapeutic patches A and B has been devised. FIG. 12 shows a method of using the combination of the therapeutic patches A and B.

The timing of removing these used therapeutic patches is as follows: about 2 days later for the therapeutic patch A and about 3 days later for the therapeutic patch B. The same applies to the combination of the therapeutic patches A and B. It is important that if itching or prickling feeling appear continuously, the therapeutic patches be removed irrespective of a time and days for which they have been used. Further, if none of the conditions appears, the metal grains and crushed stones in the sheet are pressed from above the sheet, and the patches are removed if prickling feeling appears. Even if prickling feeling does not appears, the patches should be removed within 5 days from the hygienic point of view.

EXAMPLES

Hereinafter, examples of the present invention are described by way of clinical examples, and the present invention is described more specifically. However, the present invention is not limited thereto, and can be variously changed in design to such a degree as not to deviate the technical idea of the present invention.

Clinical Example 1

(Object to be Treated)

Eighty patients suffering from knee pain (including chronic and acute pain) (average age: 50.9, male/female: 24/56) were selected at random and were classified into a metal group (Therapeutic patch B: a gold-plated iron was used as metal in a polygonal pyramid shape with a maximum diameter of 5 mm and a height of 2 mm at the center of a circular sheet of about 3.5 cm), and a non-metal group at random.

(Therapeutic Method)

The metal group and the non-metal group each included 40 patients suffering from knee pain. Sites to be treated were set to be a tender area and an induration present in the periphery of a knee and a femoral region in both the metal group and the non-metal group. As treatment methods, 10 minutes of low frequency treatment and 10 minutes of massage, and the presence or absence of metal grains were used. In order to evaluate therapeutic effects on knee pain objectively, a therapeutic method was set to be constant. Further, the difference in therapeutic effects were studied by setting a non-metal particle group as a control group and conducting treatment under the same conditions as those of the metal group.

The treatment was conducted for 3 days continuously, the two groups were subjected to statistical analysis using a visual analyze scale (VAS), and the therapeutic effects were determined at a risk rate of 1% or less.

(Therapeutic Effects)

The VAS of the patients suffering from knee pain was decreased from an average of 65.8±8.4 before the treatment to an average of 14.3±12.0 after the continuous treatment for 3 days in the metal group of the present invention (average age: 56.9, male/female: 13/27), and thus, therapeutic effects were recognized with a significant difference ($P<0.01$).

The VAS was decreased from an average of 63.5±10.4 before the treatment to an average of 45.6±10.3 after the continuous treatment for 3 days in the non-metal group (average age: 45.0, male/female: 11/29), and thus, a significant difference was not recognized.

From the foregoing, the treatment of attaching metal grains used in the metal group to the tender area up to a boundary thereof and/or the entire induration was recognized to have a sufficient effect. Substantially same effects were confirmed using titanium, germanium, and stainless steel, in addition to gold.

TABLE 1

Therapeutic effects

GROUP A (WITH PATCH)

MEASUREMENT OF THERAPEUTIC EFFECTS
- BEFORE TREATMENT VAS: 0 —— 65.8 —— 100 (mm)
- AFTER INITIAL TREATMENT
- AFTER THREE CONTINUOUS TREATMENTS: 14.3

GROUP B (WITHOUT PATCH)

MEASUREMENT OF THERAPEUTIC EFFECTS
- BEFORE TREATMENT VAS: 0 —— 63.5 —— 100 (mm)
- AFTER INITIAL TREATMENT
- AFTER THREE CONTINUOUS TREATMENTS: 45.6

THERAPEUTIC EFFECTS

SIGNIFICANT DIFFERENCE (T-TEST)

METAL GROUP: VAS (mm), $P < 0.05$, BEFORE AFTER TREATMENT GROUP A — PRESENT ($P < 0.01$)

NON-METAL GROUP: VAS (mm), BEFORE AFTER TREATMENT GROUP B — ABSENT (−)

| | AVERAGE BEFORE TREATMENT | AVERAGE AFTER THREE CONTINUOUS TREATMENTS | SIGNIFICANT DIFFERENCE |
|---|---|---|---|
| GROUP A | 65.8 ± 8.4 | 14.3 ± 12.0 | PRESENT ($P < 0.01$) |
| GROUP B | 65.5 ± 10.4 | 45.6 ± 10.3 | ABSENT (−) |

Clinical Example 2

Table 2 shows the results obtained by conducting treatment for pain in other parts of a body in the same way as in knee pain.

In the same way as in knee pain, the treatment of attaching metal grains used in the metal group of Clinical Example 1 to the tender area up to a boundary thereof and/or the entire induration was recognized to have a sufficient effect (Table 2). See data difference in significance of 1% and data after the treatment of lumbar hernia.

TABLE 2

Therapeutic effects on other pain

| | \<Name of disease\> | | | |
|---|---|---|---|---|
| | Sciatica | Lumbar hernia | Pain in cervical part | Headache |
| \<Metal group\> | | | | |
| Average before treatment | 58.7 ± 13.7 | 53.6 ± 22.8 | 62.3 ± 19.2 | 68.8 ± 18.7 |
| Average after three treatments | 17.3 ± 13.4 | 12.3 ± 20.4 | 21.2 ± 18.1 | 18.0 ± 15.3 |
| Significant difference | Present ($P < 0.05$) | Present ($P < 0.05$) | Present ($P < 0.05$) | Present ($P < 0.01$) |
| \<Non-metal group\> | | | | |
| Average before treatment | 56.5 ± 13.1 | 45.5 ± 15.1 | 60.2 ± 20.3 | 65.5 ± 18.2 |
| Average after three treatments | 38.4 ± 12.6 | 34.3 ± 27.7 | 44.5 ± 19.5 | 49.3 ± 22.5 |
| Significant difference | Absent (—) | Absent (—) | Absent (—) | Absent (—) |

| | Name of disease | | | |
|---|---|---|---|---|
| | Pain in cubital joint | Sports external injury/ disorders | Pain in shoulder joint | Pain in ankle joint |
| \<Metal group\> | | | | |
| Average before treatment | 56.1 ± 18.9 | 60.6 ± 28.8 | 60.3 ± 16.4 | 56.8 ± 14.3 |
| Average after three treatments | 11.1 ± 11.8 | 19.3 ± 22.4 | 11.8 ± 13.2 | 16.1 ± 11.5 |
| Significant difference | Present ($P < 0.01$) | Present ($P < 0.05$) | Present ($P < 0.01$) | Present ($P < 0.05$) |
| \<Non-metal group\> | | | | |
| Average before treatment | 53.5 ± 19.3 | 59.5 ± 25.1 | 58.1 ± 20.2 | 53.5 ± 13.3 |
| Average after three treatments | 38.4 ± 12.2 | 41.3 ± 27.7 | 37.0 ± 13.2 | 38.8 ± 15.7 |
| Significant difference | Absent (—) | Absent (—) | Absent (—) | Absent (—) |

Clinical Example 3

Prevention of recurrence refers to the elimination of tenderness and the complete flexing of an induration. In the case of an induration, pain is not caused depending upon the use frequency even when the induration is present. This is because pain is not caused as long as an excess load is not applied to an induration part. Further, in the case where strong tenderness remains even if pain (subjective pain) is alleviated, there is a high possibility of recurrence when the treatment is stopped. No recurrence is recognized when no pain is caused by pressing strongly with a bar as well as a finger.

According to the therapeutic method of the present invention shown in Clinical Examples 4 and 5, a recurrence ratio was 26% (i.e., 7 patients of 27 patients), and a healing ratio was 74% (i.e., 20 patients of 27 patients). This is a remarkable effect, showing a low recurrence ratio, compared with the result in which pain is alleviated in 22.4% of the patients and pain remains the same in 77.6% of the patients according to the conventional therapeutic method conducted with respect to 17,000,000 patients (The Japanese Society for the Study of Chronic Pain Vol. 25, No. 1, 2006. p 40, Miyazaki).

Clinical Example 4

A tender area maximum edge (boundary) and an induration part shown in FIG. 9A were specified by pressing a patient (in her forties, female) complaining of waist pain with a pressing bar (FIG. 7) and a finger, and a plurality of the patches A of the present invention (rectangular sheets of 12 cm×7 cm with semi-disc shape fine grains (gold-plated iron) with a diameter of about 1.3 mm adhering thereto in a lattice shape at an interval of about 8 mm) were attached to the surface of a skin so as to cover the entire boundary. Further, patches B (circular sheets with a diameter of about 3 cm with a conical grain (gold-plated iron) with a maximum diameter of 5 mm and a height of 2 mm adhering to the center thereof) were attached to the induration part so that tip end sides were adjacent to and overlapped with each other to cover the entire induration part so as to minimize a gap. Immediately after the attachment, pain was alleviated, and as a result of the attachment for one week, waist pain was recovered completely. After about 6 months, the patient went to hospital again, and no recurrence was recognized.

Clinical Example 5

A maximum edge (boundary) and a site of pain in which a patient (in her fifties, female) feels strong pain shown in FIG. 8 were specified by pressing the patient complaining of knee pain with a pressing bar (FIG. 7) and a finger, and a plurality of the patches A using the crushed stones of the present invention (rectangular sheets of 12 cm×7 cm with crushed stones (sedimentary stone) with a diameter of about 1 to 2 mm adhering randomly to the overall surface thereof) were attached to the surface of a skin so as to cover the entire boundary. Further, patches B using crushed stones (circular sheets with a diameter of about 4 cm with crushed stones (sedimentary stone) with a diameter of 2 to 5 mm adhering to the center thereof) were attached to the induration part so that the patches B were adjacent to and overlapped with each other to cover the entire induration part so as to minimize a gap. Immediately after the attachment, pain was alleviated, and as a result of the attachment for one week, knee pain was recovered completely. After about 6 months, the patient went to hospital again, and no recurrence was recognized.

Clinical Example 6

VAS and MDS data analysis: pain eliminating test by the attachment of metal grains of the therapeutic patches B overlapped with and adjacent to each other to cover the entire pain generation area (maximum edge: boundary) so as to minimize a gap
VAS: Visual Analog Scale (minimum: 0%, maximum: 100%)
MDS: Multi Dimensional Scale
Material provided by Super Medical Laboratory, Analysis, The University of Electro-Communications, emeritus professor, Kazuyoshi Sakamoto
(Object to be Treated)
Incoming patients in their teens to seventies were treated in the order of incoming, and the relationship between the aspects (sense, affectivity, evaluation) of MDS pain and the level and VAS was investigated.

Treatment sites were 108 cases in total including 22 cases of pain in a cervical part, 16 cases of pain in a shoulder (including a shoulder blade), 6 cases of a superior member (upper arm part to maniphalanx), 23 cases of pain in waist, 9 cases of pain in backside (pain in a hip joint), and 32 cases of an inferior member (femoral region to pain in a leg part).

Figure 13:
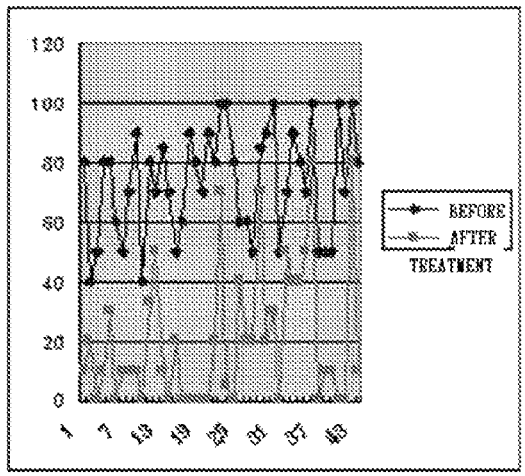
FIG. 13A is a graph illustrating VASs (first time) before and after treatment.
FIG. 13B is a graph illustrating VASs (third time) before and after treatment.
Figure 13:
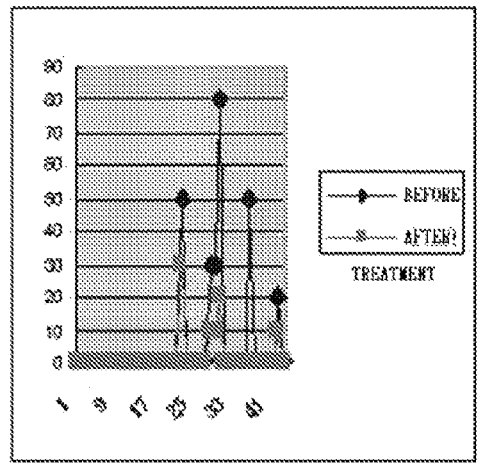

The results were as follows. VASs (1st time) before and after the treatment, a VAS average value: 73.3 before the treatment and 20.4 after the treatment; VAS standard deviation: 18.1 before the treatment and 23.5 after the treatment (FIG. 13A); VASs (3rd time) before and after the treatment, VAS average value, 6.0 before the treatment and 1.9 after the treatment; and VAS standard deviation: 16.9 before the treatment and 5.9 after the treatment (FIG. 13B). Further, the levels of the sense, affectivity, and evaluation by MDS were indicted in 1 to 5 stages. The results were as follows. Sense (1 hot and numbness, 2 prickling, 3 piercing, 4 burning, 5 pulling pain); affectivity (2 frightening, 3 scary and anxiety, 4 being awed, 5 extremely painful); evaluation (2 being irritated, 3 being acute, 4 difficult to stand, 5 agonizing); total sense at the first time before the treatment: 159, total affectivity: 29, total evaluation: 30; third time after the treatment: total sense 13, total affectivity 6, and total evaluation 0. It was found from the above that emotional distress is alleviated and internal care can also be performed along with the elimination of subjective pain of patients. Further, unlike actual pain that is not understood only with VAS, it was found that there are sensuous pain and emotional pain. It seems that the following phenomena are taking place in a number of patients who have lived together with pain for a long period of time. That is, the patients feel like having pain in spite of the fact that there is actually no pain, the patients are afraid that pain is caused again, and brain sense is unlikely to work after the rapid elimination of pain.

As described above in detail, the present invention provides a skin patch for treating pain by compressing with metallic grains or crushed stones a tender area and/or an entire induration by a treatment method in accordance with a classification of the cause of pain, based on the finding of the presence of a geographical tender area and/or the presence of an induration on a skin, determined after clarifying a pain site by pressing a skin with a pressing bar or fingers (first to fourth fingers) to classify the cause of pain.

Thus, even in the case where there is a shift between a part in which a patient complains of pain subjectively and a part which causes pain objectively, the neurological disorder, deterioration, or damage, and muscle induration are recovered effectively and quickly, and the accompanying pain and other various conditions can be ameliorated.

Accordingly, a period for treating pain can be shortened and the recurrence can be prevented, and the economical and physical burden on a patient are alleviated, which also leads to the reduction in medical fee.

Further, the patch A, the patch B, and the combination of the patches A and B of the present invention are small and light, and hence, are convenient for carrying in the case of participating in sports, travel, etc. Further, the patches can be placed in a first-aid box and hence can be stored easily.

As the metal grains of the present invention can be used semipermanently, the metal grains can be re-used, using a new sheet member when the adhesive strength of the sheet member is degraded.

What is claimed is:
1. A skin patch for treating pain against a wide area of at least one of tenderness and induration which is a low or shallow level injury, wherein the skin patch has a sheet-shape of a size of 5 to 15 cm on a side, in which a plurality of fine grains each having a particle diameter of 0.1 to 1.8 mm are adhered to a surface of the sheet-shape, an interval between the plurality of fine grains is 4 to 8 mm, the plurality of fine grains are arranged in a square-shaped form, and the skin patch is attachable to at least one of a tender area and an induration which is confirmed by pressing and is extending geographically, so as to fully cover at least one of the tender area and the induration which is a low or shallow level injury.

2. A skin patch kit comprising: a skin patch A and a skin patch B for treating pain against at least one of an area of tenderness and induration which is a deep level injury, wherein the skin patch B has a round-sheet-shape of a maximum length of 1.5 to 3 cm, in which a pyramid-shaped grain having a particle diameter of 5 to 10 mm and a height of 1 to 5 mm is adhered to a surface of the round-sheet-shape, the skin patch B is attachable to at least one of a tender area and an induration over the skin patch A, wherein the skin patch A has a sheet-shape of a size of 5 to 15 cm on a side, in which a plurality of fine grains each having a particle diameter of 0.1 to 1.8 mm are adhered to a surface of the sheet-shape, an interval between the plurality of fine grains is 4 to 8 mm, the plurality of fine grains are arranged in a square-shaped form, and the skin patch A is attachable to at least one of a tender area and an induration which is confirmed by pressing and is extending geographically, so as to fully cover at least one of the tender area and the induration which is a low or shallow level injury, wherein the at least one of a tender area and induration is confirmed by pressing after being treated by patching of the skin patch A, so as to fully cover at least one of the tender area and the induration which is a deep level injury, wherein the skin patch A and the skin patch B being overlapped with and adjacent to each other, and the skin patch A and the skin patch B are used as a kit.

3. A skin patch for treating pain according to claim 1, which is confirmed at the at least one of a tender area and an induration by pressing with a pressing bar.

4. A skin patch for treating pain according to claim 2, which is confirmed at the at least one of a tender area and an induration by pressing with a pressing bar.

5. A skin patch for treating pain according to claim 3, wherein the pressing bar has spherical shape or semi-spherical shape at both ends, and the pressing bar has a diameter of 4 to 8 mm, and a length of 20 to 25 cm.

6. A skin patch for treating pain according to claim 4, wherein the pressing bar has spherical shape or semi-spherical shape at both ends, and the pressing bar has a diameter of 4 to 8 mm, and a length of 20 to 25 cm.

7. A skin patch kit comprising a skin patch A for treating pain against a wide area of at least one of tenderness and induration which is a low or shallow level injury and a skin patch B for treating pain against at least one of an area of tenderness and induration which is a deep level injury, wherein the skin patch A has a sheet-shape of a size of 5 to 15 cm on a side, in which a plurality of fine grains each having a particle diameter of 0.1 to 1.8 mm are adhered to a surface of the sheet-shape, an interval between the plurality of fine grains is 4 to 8 mm, and the plurality of fine grains are arranged in a square-shaped form, and the skin patch A is attachable to at least one of a tender area and an induration, which is confirmed by pressing and is extending geographically, so as to fully cover at least one of the tender area and the induration which is a low or shallow level injury, and wherein the skin patch B has a round-sheet-shape of a maximum length of 1.5 to 3 cm, in which a pyramid-shaped grain having a particle diameter of 5 to 10 mm and a height of 1 to 5 mm is adhered to a surface of the round-sheet-shape, the skin patch B is attachable to at least one of a tender area and an induration over the skin patch A, wherein the at least one of a tender area and induration is confirmed by pressing after being treated by patching with the skin patch A, so as to fully cover at least one of the tender area and the induration which is a deep level injury, wherein the skin patch A and the skin patch B being overlapped with and adjacent to each other.

* * * * *